(12) United States Patent
Younghouse et al.

(10) Patent No.: US 9,958,420 B2
(45) Date of Patent: May 1, 2018

(54) SYNTHETIC DATA COLLECTION METHOD FOR FULL MATRIX CAPTURE USING AN ULTRASOUND ARRAY

(71) Applicant: BWXT Technical Services Group, Inc., Lynchburg, VA (US)

(72) Inventors: Steven J Younghouse, Forest, VA (US); Daniel T MacLauchlan, Lynchburg, VA (US); Nicholas J Borchers, Blacksburg, VA (US)

(73) Assignee: BWXT Technical Services Group, Inc., Lynchburg, VA (US)

( * ) Notice: Subject to any disclaimer, the term of this patent is extended or adjusted under 35 U.S.C. 154(b) by 228 days.

(21) Appl. No.: 13/760,172

(22) Filed: Feb. 6, 2013

(65) Prior Publication Data

US 2014/0219059 A1    Aug. 7, 2014

(51) Int. Cl.
*G01S 15/89* (2006.01)
*G01N 29/26* (2006.01)
*G01S 7/52* (2006.01)

(52) U.S. Cl.
CPC ........ *G01N 29/262* (2013.01); *G01S 7/52085* (2013.01); *G01S 15/8915* (2013.01); *G01N 2291/106* (2013.01)

(58) Field of Classification Search
USPC .......................................................... 367/11
See application file for complete search history.

(56) References Cited

U.S. PATENT DOCUMENTS 4,550,606 A * 11/1985 Drost .............................. 73/626
4,596,145 A *  6/1986 Smith et al. ................... 73/626
4,694,434 A *  9/1987 von Ramm et al. .............. 367/7
5,060,651 A * 10/1991 Kondo et al. ................. 600/443
5,490,512 A *  2/1996 Kwon et al. .................. 600/447
5,655,535 A *  8/1997 Friemel et al. ............... 600/443
(Continued)

FOREIGN PATENT DOCUMENTS

CN           1766672 A        5/2006
CN         101809459 A        8/2010
WO    WO 2008033528 A2 *     3/2008    ............. G10K 11/34

OTHER PUBLICATIONS

International Search Report for PCT/US2014/012349.*
(Continued)

*Primary Examiner* — James R Hulka
(74) *Attorney, Agent, or Firm* — Nelson Mullins Riley & Scarborough LLP

(57) ABSTRACT

A method for efficiently achieving full-matrix ultrasonic data capture which includes the steps of providing an ultrasound array apparatus, the ultrasound array apparatus further comprising a probe, collecting data over a plurality of inspection locations, generating a plurality of data matrices, each of the data matrices reflecting data collected at the locations, and collecting, initially, a subset of a quantity of data needed for reconstruction of each of the inspection locations. In the method, as the probe moves from collection location to collection location, a data matrix at a prior collection location is gradually filled in as the probe moves to subsequent collection locations. In certain embodiments physical scanning of a probe with few elements is replaced by electronically scanning using an array with many elements.

5 Claims, 3 Drawing Sheets

(56) References Cited

U.S. PATENT DOCUMENTS

| | | | |
|---|---|---|---|
| 5,894,646 A * | 4/1999 | Hanafy et al. | 29/25.35 |
| 5,911,221 A * | 6/1999 | Teo | 600/447 |
| 6,279,399 B1 * | 8/2001 | Holm | 73/626 |
| 6,360,027 B1 * | 3/2002 | Hossack et al. | 382/294 |
| 6,755,787 B2 * | 6/2004 | Hossack et al. | 600/447 |
| 7,780,597 B2 * | 8/2010 | Panda et al. | 600/437 |
| 8,303,505 B2 * | 11/2012 | Webler et al. | 600/447 |
| 2003/0097068 A1 * | 5/2003 | Hossack et al. | 600/443 |
| 2004/0174773 A1 * | 9/2004 | Thomenius | B06B 1/0292 367/174 |
| 2005/0057284 A1 * | 3/2005 | Wodnicki | A61B 8/13 327/100 |
| 2007/0167801 A1 * | 7/2007 | Webler et al. | 600/459 |
| 2009/0209859 A1 * | 8/2009 | Tsujita | A61B 8/00 600/445 |
| 2010/0217127 A1 * | 8/2010 | Roundhill | A61B 8/08 600/444 |

OTHER PUBLICATIONS

Harvey, G., Tweedie, A., Carpentier, C., Reynolds, P., Thompson, D. O., & Chimenti, D. E. (Jun. 2011). Finite element analysis of ultrasonic phased array inspections on anisotropic welds. In AIP Conference Proceedings—American Institute of Physics (vol. 1335, No. 1, p. 827).*

International Search Report and Written Opinion dated Apr. 15, 2014 for International Application No. PCT/US2014/012349.

European Search Report dated Sep. 28, 2016 for EP Application No. 14748692.2.

Holmes, et al: "Advanced post-processing for scanned ultrasonic arrays: Application to defect detection and classification in non-destructive evaluation", Ultrasonics, IPC Science and Technology Press Ltd. Guilford, GB, vol. 48, No. 6-7, Nov. 1, 2008, pp. 636-642.

First Australian Examination Report dated Jul. 25, 2017 for Australian Application No. 2014215717.

Chinese Office Action dated Jan. 23, 2017 for Chinese Application No. 201480012594.6.

* cited by examiner

Step 1

Step 2

SYNTHETIC DATA COLLECTION METHOD FOR FULL MATRIX CAPTURE USING AN ULTRASOUND ARRAY

FIELD AND BACKGROUND OF THE INVENTION

1. Field of the Invention

The present invention relates generally to the field of data collection, and in particular to a new and useful method for achieving full matrix capture and processing of waveform data by employing an ultrasound array apparatus.

2. Description of the Related Art

In ultrasonic testing, very short ultrasonic pulse-waves with center frequencies ranging typically from 0.1 to 15 MHz and, occasionally, up to 50 MHz are launched into materials to detect internal flaws or to characterize materials. The technique is also commonly used to determine the thickness of a tested object, for example, to monitor pipe wall corrosion.

Ultrasonic testing is often performed on steel and other metals and alloys, though it can also be used on concrete, wood and composites, albeit with lower resolution. It is a form of non-destructive testing used in many industries.

Two basic methods of receiving the ultrasound waveform are pulse-echo and pitch-catch. In pulse-echo mode the transducer performs both the sending and the receiving of the pulsed waves as the "sound" is reflected back to the device. The reflected ultrasound comes from an interface such as the back wall of the object or from an imperfection within the object. The diagnostic machine typically displays these results in the form of a signal with amplitude representing intensity of the reflection and arrival time of the reflection representing distance. In pitch-catch mode separate transducers are employed to transmit and receive the ultrasound.

There are a number of benefits to ultrasound testing. This testing method provides high-penetrating power, which allows the detection of flaws deep in the part being analyzed. It is also a high sensitivity form of testing, permitting the detection of extremely small flaws. Generally only one surface needs to be accessible for ultrasound testing. The method provides greater accuracy than other nondestructive methods in determining the depth of internal flaws and the thickness of parts with parallel surfaces. It provides some capability of estimating the size, orientation, shape and nature of defects. It is generally nonhazardous to operations or to nearby personnel and has no effect on equipment and materials in the vicinity. It is also capable of portable as well as highly-automated operation.

One type of ultrasound testing is known as phased array ultrasound. For this type of testing the probe(s) are comprised of a plurality (array) of elements, each of which can transmit and/or receive ultrasound independently. By combining the transmitted waves from each individual element a composite sound beam is created. This beam may be steered and/or focused in an arbitrary manner by applying short time delays across the elements and then firing the elements together. In an analogous manner a receive array may be set to be sensitive to incoming ultrasound from a particular angle and/or focal depth by applying a set of short delays across elements and subsequently adding together contributions from all elements.

Matrix capture of ultrasonic information is a powerful technique for inspection which uses the same array probes as phased array ultrasound. The method is distinct, however. Matrix capture is achieved, for example, by firing each array element in succession and recording the received waveforms at all elements for each firing. The resulting collected data at a given inspection location forms a matrix of waveforms for which each waveform is associated with one transmit-receive element pair. By acquiring all data for every transmit/receive element pair over the array, virtual ultrasonic scans at arbitrary angles can be reconstructed at any time after data has been collected by applying the appropriate set of short delays to the recorded waveforms and then adding all signals together (using a computer, for instance).

Matrix capture is identified as distinct from phased array in the following manner. In the phased array method, at a given inspection location the appropriate set of short delays is applied to all waveforms during transmit and receive phases, and at that time waveforms from all array elements are summed together. Only the final result is stored. In the matrix capture method all waveforms corresponding to every combination of transmit and receive element at each inspection location are stored in a data matrix. At any subsequent time in post-processing the appropriate set of short delays are applied to the stored waveforms and all waveforms in the matrix are summed together in order to effectively create a steered and/or focused beam of ultrasound.

Known matrix capture techniques, however, have an inherent and significant disadvantage, namely the need for storing a large amount of data. All waveforms for all transmit/receive pairs must be stored for every scan location.

By way of an illustration, each waveform typically requires 1000 time points to be collected, each point requiring one byte. For a 32-element array this means that $(32)^2$, or 1024, waveforms must be collected. At 1000 bytes each, this collection results in 1 MB of data stored for each scan location. Even a small scan will require on the order of 100 times 100, or 10,000, scan locations. This collection of data will result in total data storage of about 10 GB. For the case of a pulse-echo inspection with a probe containing m elements the number of waveforms that must be collected per scan location, including reciprocity considerations, is:

$$\text{Number of waveforms per inspection location(pulse-echo)} = \frac{m \cdot (m+1)}{2}.$$

This requirement strains data storage needs, and also can place a practical limitation on scan speed because it can be difficult to rapidly move so much data.

Gains in efficiency can be realized by a method in which scan and/or index increments are set equal to element pitch or unit fractions thereof. In this case a large fraction of the collected data at one location is (theoretically) identical with data collected at neighboring locations.

One illustrative example involves a situation in which the array probe is operating in pulse-echo mode and has three elements. The probe will be moved to three separate positions along the same direction as the ultrasonic array. At any given position, in order to accumulate data from all transmit-receive pairs with a standard method of data capture then $$\frac{m \cdot (m+1)}{2} = \frac{3 \cdot 4}{2} = 6$$

waveforms must be recorded. Additionally, each of the three elements must be fired once. In order to collect all data for the three probe positions a total of 9 element firings are needed and 18 waveforms must be collected.

This situation is illustrated in FIG. 1, in the section marked "Standard Data Collection." A set of tables are shown, each representing the data matrices for a probe at subsequent inspection locations (shown in the upper left) corresponding to a 3-element array moving in increments of one element pitch. Tables from left to right represent data matrices which need to be filled in each subsequent location (A, B, C). Tables from top to bottom represent these same arrays at subsequent probe locations (A, B, C). The data required at each location is a set of waveforms corresponding to each transmit-receive pair. The letters in the tables represent the probe location at which data is collected. For standard collection, at each probe location (A, B, and C), all data for reconstruction at that respective location is collected.

In the case where the probe is moved along the array direction at a step size equal to the element pitch, if the elements are fired 9 times and 18 waveforms are collected then much of the data is redundant.

Thus, a need exists for a method of capture of waveform data that is efficient and overcomes the above deficiencies, including, but not limited to, redundancies and strain on storage capacity.

SUMMARY OF THE INVENTION

The present invention addresses known deficiencies in the art and is drawn to a new and efficient method of data collection that effectively employs ultrasound technology.

Accordingly, one aspect of the present invention is to provide a means for achieving full matrix capture by efficiently employing an ultrasound array apparatus.

Embodiments of the present invention provide a method for efficiently achieving full-matrix ultrasonic data capture which includes the steps of providing an ultrasound array apparatus, the ultrasound array apparatus further comprising a probe, moving the probe over a plurality of collection locations, generating a plurality of data matrices, each of the data matrices reflecting data collected at the locations, and collecting, initially, a subset quantity of data needed for reconstruction of each of the collection locations. In the method, as the probe moves from one collection location to the next, a data matrix at a prior collection location is gradually filled in as the probe moves to subsequent collection locations.

Accordingly, one aspect of the present invention is drawn to a method for efficiently achieving full-matrix ultrasonic data capture comprising: (a) providing an ultrasound array apparatus, the ultrasound array apparatus comprising a probe, the probe adapted for positioning over a test piece; (b) collecting data over a plurality of locations; (c) generating a plurality of data matrices, each of the data matrices reflecting data collected at the locations; (d) collecting, initially, a subset of a quantity of data needed for reconstruction at each of the locations; and (e) collecting data from location to location, gradually filling in a data matrix at a prior location as the probe moves to subsequent locations.

Accordingly, another aspect of the present invention is drawn to a method for efficiently achieving full-matrix ultrasonic data capture comprising: (A) providing a two-dimensional ultrasound array apparatus, the ultrasound array apparatus comprising a probe, the probe adapted for scanning and the probe comprising scan increments and nominal scan boundaries; (B) moving the probe over a plurality of inspection locations; (C) generating a plurality of data matrices, each of the data matrices reflecting data collected at the inspection locations; (D) collecting, initially, a subset of a quantity of data needed for reconstruction at each of the inspection locations; and (E) as the probe moves from inspection location to inspection location, gradually filling in a data matrix at a prior inspection location as the probe moves to subsequent inspection locations.

Inspection locations may correspond to collection locations but are not necessarily the same. For example, if only sparse coverage is required (e.g. for component thickness mapping) then inspection locations may correspond to some subset of collection locations.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE EMBODIMENTS

Figure 1:
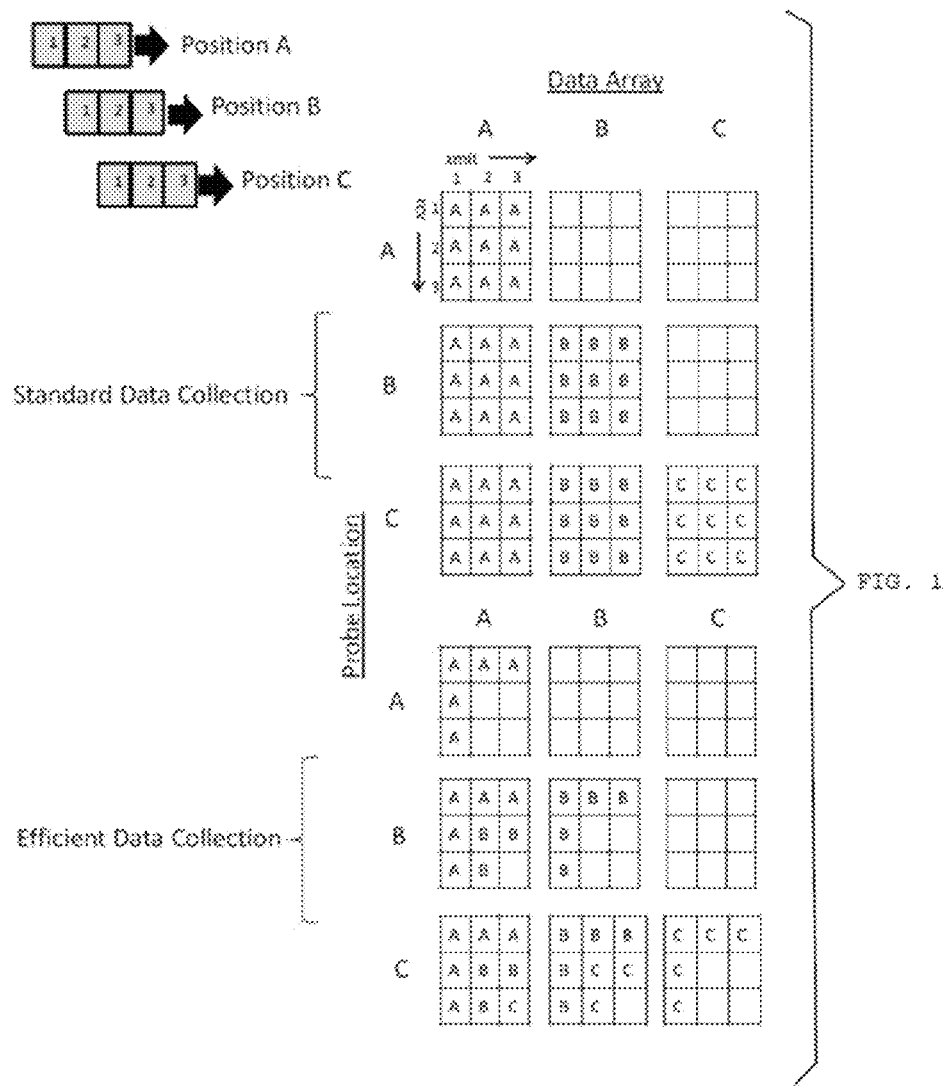
FIG. 1 is a composite schematic illustration of how an array probe operating according to the present efficient data collection method compares with standard data collection.

Referring now to the drawings, FIG. 1 illustrates, in the section identified as "Efficient Data Collection," the present, novel ultrasound data collection method. Following the "Standard Data Collection" method, in order to collect all data for the three probe positions a total of 9 element firings would be needed and 18 waveforms must be collected. According to the present "Efficient Data Collection" method only 5 element firings and 12 waveforms need to be collected in order to have all waveform data at all positions. In order for this particular implementation to be possible the probe increment must be equal to element pitch. Also, this particular implementation relies on the reciprocity principle (i.e. a signal transmitted by element x and received by element y is in principle the same as a signal transmitted by element y and received by element x). In the case of pulse-echo operation the consequence of the reciprocity principle is that the matrix is symmetrical about its diagonal; i.e. element xy is equal to element yx. At each probe location only one element is fired and all elements receive. As a result, a subset of the data needed for reconstruction at that location is collected. As the probe moves from position A to B to C, the data matrix at location A is gradually filled in. While only three firings are shown, as the probe continues to move the data matrices for locations B and C will be filled as well. Considering, for example, the data matrix at location A: as the probe moves, data from locations A, B, and C are all used to enable reconstruction at that point.

The advantage in efficiency provided by embodiments of the present invention increases as the number of elements and positions increases. For k positions along an inspection line and m elements, number of firings needed and waveforms to be collected are expressed below as Number of firings (pulse-echo)=$(k+m-1)$, and $$\text{Number of waveforms needed(pulse-echo)} = (k \cdot m) + \frac{m \cdot (m-1)}{2}.$$

So, in the situation in which a 32-element array is used and 100 data points are taken along a scan line, only 3,696 waveforms will need to be collected and only 131 element firings will be needed. This compares very favorably to the $(32 \times 33/2) \times 100 = 52,800$ waveforms that would need to be collected from 3200 firings in the absence of the presently-claimed invention, which takes advantage of data redundancy.

If the probe increment is set to a unit fraction of element pitch then the procedure outlined in paragraph 20 may still be applied. In the case that probe increment is equal to element pitch divided by L, then conceptually L arrays may be created and data will be collected for each one in turn every L scan increments. In order to fill all data matrices completely the number k of inspection locations must be evenly divisible by L. Then, for a total of k positions the number of firings necessary and number of waveforms needed are expressed in the equations below as:

Number of firings (increment is unit fraction of pitch)=$k+L \cdot (m-1)$, and

Number of waveforms(increment is unit fraction of pitch) =
$$(k \cdot m) + L \cdot \frac{m \cdot (m-1)}{2},$$

where k>L for both of the above equations.

Figure 2:
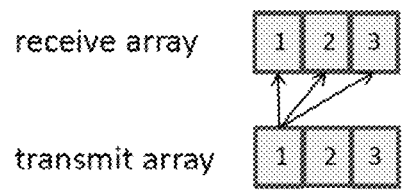
FIG. 2 is an illustration of a two-step process specific to a "pitch-catch" probe arrangement where at each collection location, in addition to the transmit element firing, the opposing element from the "catch" probe also transmits a signal and all elements from the "transmit" probe (save for the one which originally transmitted) collect the receive signals.
Figure 2:
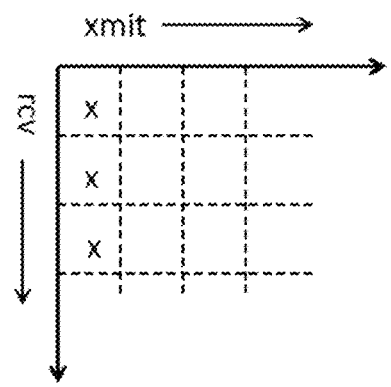
Figure 2:
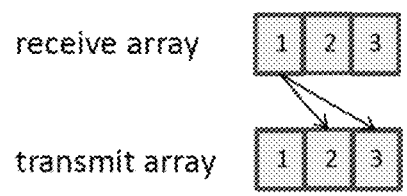
Figure 2:
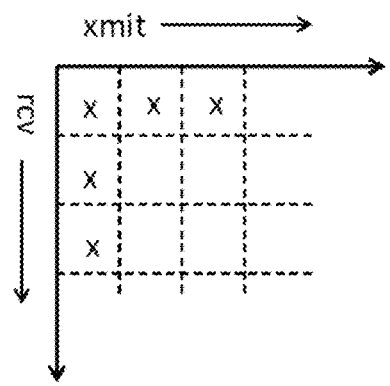

If the inspection is performed using a pitch-catch arrangement then a second step is required in order to complete the subset of data that must be collected at each location. Elements normally arranged as receivers must be adapted as transmitters as well, and conversely elements arranged as transmitters must be arranged as receivers as well. At each collection location, in addition to the transmit element firing the opposing element from the "catch" probe must also transmit a signal and all elements from the "transmit" probe (save for the one which originally transmitted) must receive the signals. This procedure is represented in FIG. 2 as a two-step process. In this manner the sub-array will be filled and collection may proceed as outlined in paragraph 20. If this arrangement is made then the total number of firings needed and total number of waveforms needed are expressed in the equations below as Number of firings (pitch-catch)=$2(k+m-1)-1$, and Number of waveforms collected (pitch-catch)=$k(2m-1)+(m-1)^2$.

In certain embodiments scan increment is equal to element pitch. In these embodiments an alternative to moving the probe along the direction of the array is to make a probe with many elements and generate a transmit and receive sequence which is equivalent to moving a smaller probe. While this requires the construction of a large array, it provides the advantage of potentially eliminating moving parts and positioning errors.

Embodiments of the present invention may also be applied in the context of two-dimensional arrays, for which gains in data storage and firing efficiency can be even more dramatic. In fact, without application of the present, novel method to improve efficiency it is likely that matrix firing would be impractical to implement for all but the smallest two-dimensional arrays using computer technology available today. For example, consider the situation of a 16-element×8-element array probe operating in pulse echo mode. Without implementation of such a technique to improve efficiency, $(16 \times 8) = 128$ firings would be needed at each probe position in order to obtain the $(128 \times 129)/2 = 8256$ waveforms. Assuming 1000 one-byte points per waveform and an array of 100 by 100 probe positions, this leads to a total data storage size of 82 GB.

Figure 3:
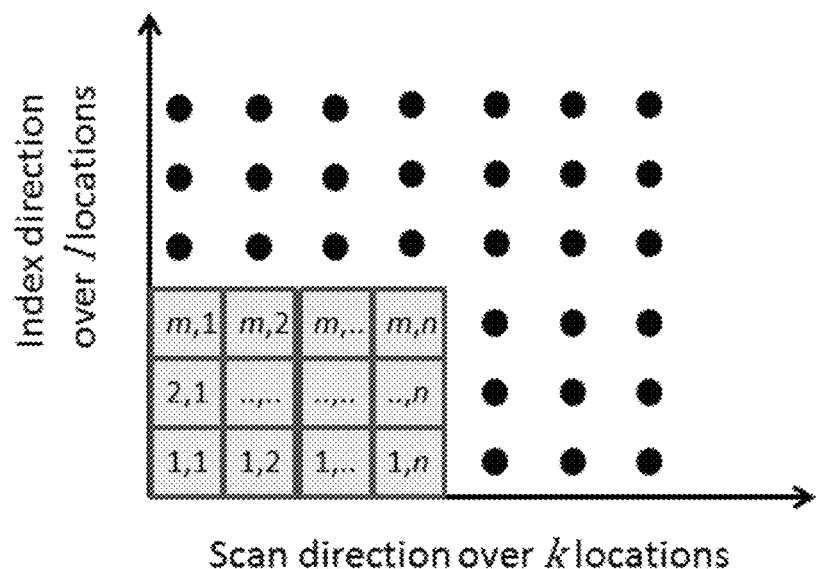
FIG. 3 is an illustration of a configuration for a two-dimensional ultrasonic array, including a representation of array indices as well as orientation with respect to scan and index axes.

By re-using data collected at different probe positions the present invention provides a very considerable savings in number of firings and data collection. Consider a raster scan along both array directions for a two-dimensional array with n elements along the scan direction and m elements along the index (or step) direction. The raster scan includes k collection locations along the scan direction and l steps. An illustration of this arrangement is provided in FIG. 3. For the (n×m)-element ultrasonic array operating in pulse-echo mode only m or n firings (whichever is smaller) are needed and $(n \cdot m)+(n-1) \cdot (m-1)$ waveforms need to be stored at each collection location. This corresponds to firing the corner element (i.e., element (1,1)) and receiving on all elements, then firing each element along the short edge of the array in turn (e.g., elements (M,1) for M=2 through m) and, for each firing, receiving on all elements along the long edge of the array (e.g., elements (1,N) where N=2 through n). (Additional waveforms will need to be recorded in order to fill data matrices near edges of the inspection grid). In one embodiment the probe will be scanned beyond the nominal scan boundaries and data will be taken such that data matrices near the boundaries are filled. The distance the probe is scanned beyond the scan boundaries is equal to the number of elements along each respective dimension minus one. Thus, if there are k scan points along the "n" dimension of the probe and l scan points along the "m" dimension of the probe, a conservative estimate of the total number of waveforms needed is shown below:

Number of waveforms (2D array)≈$(k+n-1) \cdot (l+m-1) \cdot [n \cdot m+(n-1) \cdot (m-1)]$.

This approximate formula is an overestimate of the total number of waveforms needed because fewer than $[(n \cdot m)+(n-1) \cdot (m-1)]$ waveforms will need to be collected at scan locations near the edges of the grid in order to provide a full reconstruction over the k by l grid. However, it is sufficient to demonstrate the advantage of use of this novel collection method in order to reduce data storage requirements. Returning to the 16×8 array example, this means that only 8 firings are necessary at each probe position and 233 waveforms need to be stored. For the same 100 by 100 array of probe positions this leads to total data storage of approximately $(115 \cdot 107 \cdot 233) \cdot 1000$ bytes equals approximately 3 GB which is easily achievable using the technology currently known in the art.

In another embodiment of the present invention, as it pertains to two-dimensional arrays, symmetry is exploited only along the index direction. This may be done for a variety of reasons. As examples, if positioning along the index direction cannot be performed with sufficient precision, or if the index increment cannot be set equal to element pitch along that direction, or if the scan is performed along only one direction, then symmetry cannot be exploited along the index direction. In this case significant gains can still be made by implementing the following procedure: at each scan location, all m elements for which N=1 (i.e. element (M,1) where M=1 through m) are fired in turn, and for each firing all received waveforms from all elements in the array are recorded. (Note that, when firing element(s) (M,1) where M>1, waveforms at elements (M',1) where M'<M does not need to be recorded because reciprocity considerations render it redundant.) At each scan location m firings are thus required and $$\left[(m^2 \cdot n) - \frac{m(m-1)}{2}\right]$$

waveforms must be recorded. Extra waveforms will need to be recorded at locations beyond the nominal scan grid in order to record all waveforms needed to fill all matrices at every scan location. An estimate of the total number of waveforms needed for a scan over k by l locations is:

Number of waveforms (2D array, symmetry exploited only

Number of waveforms (2D array, symmetry exploited only along scan direction) $\approx (k + n - 1) \cdot l \cdot \left[(m^2 \cdot n) - \frac{m \cdot (m-1)}{2}\right]$.

This estimate is slightly conservative because it does not account for the reduced number of waveforms which need to be collected at locations beyond the nominal range k. Returning to the example of a 16×8 array with 100×100 scan locations, the total data which needs to be stored is approximately (115·100·996)·1000 bytes equals 11.45 GB. This is still a very considerable improvement over the storage requirement of 82 GB which is required using the standard collection methodology.

The present invention provides at least three advantages. The first is reduction of data storage. This allows more files to be stored on a single drive and also allows the ability in some cases to put all scan data into system memory, which would allow instantaneous access to all scan data. The second is potential for dramatically increased scan speed. Since less data is being acquired at each position, data throughput is reduced considerably. This increase in scan speed can result in reduced inspection costs. The third advantage is the potential for cleaner data because fewer transmitter firings results in a longer time interval between firings, which means that the sound has more time to dissipate.

Alternatives to the present efficient data collection method involve collecting the full set of data at every scan location. This method results in slower scan times, potentially noisier data, and greatly increased (and in some cases impractical) storage requirements.

While a specific embodiment of the invention has been shown and described in detail to illustrate the application of the principles of the invention, it will be understood that the invention may be embodied otherwise without departing from such principles.

What is claimed is:

1. A method for efficiently achieving full-matrix ultrasonic data capture comprising:
   (A) providing a two-dimensional ultrasound array apparatus, the ultrasound array apparatus comprising a probe, the probe adapted for scanning and the probe comprising scan increments and nominal scan boundaries, wherein the two-dimensional ultrasound array apparatus has two array dimensions, an array dimension m along a long axis and an array dimension n along a short axis:
   (B) moving the probe to a first location on the test piece;
   (C) firing a first element in the short axis of the two-dimensional array and receiving data at all other elements of the array;
   (D) subsequently firing at each of the remaining further elements along the short edge of array in turn, and receiving on all elements along the long edge of the array;
   (E) moving the probe over a plurality of inspection locations in a raster scan;
   (F) repeating the steps of firing at a first element in the short axis of the two-dimensional array and receiving data at all other elements of the array, and subsequently firing at each of the remaining further elements along the short edge of array in turn, and receiving on all elements along the long edge of the array at the new inspection location.

2. The method of claim 1, wherein the array is operated in pulse-echo mode.

3. The method of claim 1, wherein the probe is scanned a predetermined distance beyond the nominal scan boundaries and the quantity of data is collected such that data matrices of the plurality of data matrices near the nominal scan boundaries are filled.

4. The method of claim 3, wherein each of the dimensions has a number of elements along a length thereof, and wherein the distance the probe is scanned beyond the nominal scan boundaries is equal to the number of elements along each respective dimension minus one.

5. The method of claim 4, wherein there are k scan points along the n dimension and l index, or step, points along the m dimension.

* * * * *